United States Patent [19]

Timmers et al.

[11] Patent Number: 5,679,816

[45] Date of Patent: Oct. 21, 1997

[54] PREPARATION OF BISCYCLOPENTADIENYL DIENE COMPLEXES

[75] Inventors: Francis J. Timmers; David D. Devore; David R. Neithamer, all of Midland, Mich.

[73] Assignee: The Dow Chemical Company, Midland, Mich.

[21] Appl. No.: 582,324

[22] Filed: Jan. 3, 1996

[51] Int. Cl.$^6$ ............................ C07F 17/00; C07F 7/00
[52] U.S. Cl. .................... 556/53; 556/11; 556/12; 556/28; 526/160; 526/943; 502/103; 502/117
[58] Field of Search .......................... 556/11, 12, 28, 556/53; 526/943, 160; 502/103, 117

[56] References Cited

U.S. PATENT DOCUMENTS

| | | | |
|---|---|---|---|
| 4,469,638 | 9/1984 | Bonnemann et al. | 260/439 CY |
| 4,556,719 | 12/1985 | Bonnemann et al. | 556/13 |
| 5,470,993 | 11/1995 | Devore et al. | 556/11 |
| 5,527,929 | 6/1996 | Timmers et al. | 556/7 |
| 5,541,349 | 7/1996 | Wilson et al. | 556/10 |
| 5,543,480 | 8/1996 | Patton et al. | 526/126 |
| 5,556,928 | 9/1996 | Devore et al. | 525/127 |

FOREIGN PATENT DOCUMENTS

| | | |
|---|---|---|
| 406135978 | 5/1994 | Japan . |
| 9604290 | 2/1996 | WIPO . |

OTHER PUBLICATIONS

Yasuda et al., Chemistry Letters, No. 4, pp. 519–522 1981.
Erker et al., Chemische Berichte, vol. 120, No. 4, pp. 507–519 Apr. 1987.
Erker et al., Chemische Berichte, vol. 115, No. 10, pp. 3300–3310 Oct. 1982.

Primary Examiner—Porfirio Nazario-Gonzalez

[57] ABSTRACT

Biscyclopentadienyl, Group 4 transition metal complexes containing a conjugated diene ligand group wherein the diene is bound to the transition metal either in the form of σ-complex or a π-complex are readily prepared by reacting in any order:

a) a Group 4 metal salt corresponding to the formula $M'X_3$ or $M''X_4$, or a Lewis base adduct thereof, b) a conjugated diene, D', c) a reducing agent, and d) a compound of the formula: $CpM^*$ or $(Cp\text{-}Cp)M^*n_n$, wherein.

M' is titanium, zirconium or hafnium in the +3 formal oxidation state;

M" is titanium, zirconium or hafnium in the +4 formal oxidation state;

X is a halide, $C_{1\text{-}6}$ hydrocarbyloxy or di($C_{1\text{-}6}$ hydrocarbyl) amido group;

D' is an uncoordinated diene having the same number of carbons as D and the same substitution pattern as D;

M* is a Group 1 or 2 metal cation, a Grignard reagent cation or a tri($C_{1\text{-}4}$ hydrocarbyl)silyl group; and n is 1 when M* is a Group 2 metal cation and n is 2 when M* is a Group 1 metal cation, a Grignard reagent cation, or a trihydrocarbylsilyl group with the proviso that reagents a), and d) are not contacted with one another in the absence of reagent c).

6 Claims, No Drawings

PREPARATION OF BISCYCLOPENTADIENYL DIENE COMPLEXES

This invention relates to a process for preparing certain biscyclopentadienyl Group 4 transition metal complexes possessing diene ligands. The complexes are valuable commercial polymerization catalysts for use in preparing polyolefins, especially crystalline polypropylene.

The preparation and characterization of certain biscyclopentadienyl ($Cp_2$) zirconium and hafnium diene complexes is described in the following references: Yasuda, et al., *Organometallics*, 1982, 1, 388 (Yasuda I); Yasuda, et al. *Acc. Chem. Res.*, 1985, 18 120 (Yasuda II); Erker, et al., *Adv. Organomet. Chem.*, 1985, 24, 1 (Erker I); Erker et al. *Chem. Ber.*, 1994, 127, 805 (Erker II); and U.S. Pat. No. 5,198,401. The present metal complexes were first disclosed in U.S. application Ser. No. 08/284,925, filed Aug. 2, 1994, of which U.S. Ser. No. 08/481,791, filed Jun. 7, 1995 is a continuation-in-part application, the teachings of which are hereby incorporated by reference.

U.S. Pat. No. 5,470,993 disclosed monocyclopentadienyl diene complexes with titanium or zirconium in which the metal is in the +2 formal oxidation state. Such metal complexes were formed by contacting a metal dihalide with a source of the cyclopentadienyl dianion ligand, a reducing agent and the neutral diene compound in any order.

SUMMARY OF THE INVENTION

The present invention relates to a process for preparing metal complexes containing two cyclopentadienyl groups or substituted cyclopentadienyl groups, said complex corresponding to the formula:

(Cp)$_2$MD wherein:

M is titanium, zirconium or hafnium in the +2 or +4 formal oxidation state;

Cp independently each occurrence is a substituted or unsubstituted cyclopentadienyl group bound in an $\eta^5$ bonding mode to the metal, said substituted cyclopentadienyl group being substituted with from one to five substituents independently selected from the group consisting of hydrocarbyl, silyl, germyl, halo, cyano, hydrocarbyloxy, siloxy, and mixtures thereof, said substituent having up to 20 nonhydrogen atoms, or optionally, two such substituents (except cyano or halo) together cause Cp to have a fused ring structure, or together form one or two linking moieties joining the two Cp groups;

D is a stable, conjugated diene ligand, optionally substituted with one or more hydrocarbyl groups, silyl groups, hydrocarbylsilyl groups, silylhydrocarbyl groups, or mixtures thereof, said D having from 4 up to 40 nonhydrogen atoms and forming a π-complex with M when M is in the +2 formal oxidation state, and forming two σ-bonds with M when M is in the +4 formal oxidation state, said process comprising contacting in any order:

a) a Group 4 metal salt corresponding to the formula M'X$_3$ or M"X$_4$, or a Lewis base adduct thereof,
b) a conjugated diene, D',
c) a reducing agent, and
d) a compound of the formula: CpM* or (Cp-Cp)M*$_n$, wherein, M' is titanium, zirconium or hafnium in the +3 formal oxidation state;

M" is titanium, zirconium or hafnium in the +4 formal oxidation state;

X is a halide, $C_{1-6}$ hydrocarbyloxy or di($C_{1-6}$ hydrocarbyl) amido group;

D' is an uncoordinated diene having the same number of carbons as D and the same substitution pattern as D;

M* is a Group 1 or 2 metal cation, a Grignard reagent cation or a tri($C_{1-4}$ hydrocarbyl)silyl group; and n is 1 when M* is a Group 2 metal cation and n is 2 when M* is a Group 1 metal cation, a Grignard reagent cation, or a trihydrocarbylsilyl group with the proviso that reagents a), and d) are not contacted with one another in the absence of reagent c).

Thus, suitable processes entail:contacting components a), b) and c), and thereafter contacting the resulting product with component d), contacting components b) and c), contacting the resulting product with component a) and thereafter contacting the resulting product with component d), or contacting all four components simultaneously.

In the diene complexes in which M is in the +2 formal oxidation state, the diene is associated with M as a π-complex in which the diene normally assumes an s-trans configuration or an s-cis configuration in which the bond lengths between M and the four carbon atoms of the conjugated diene are nearly equal (Δd as defined hereafter ≥−0.15 Å) whereas in the complexes in which M is in the +4 formal oxidation state, the diene is associated with the transition metal as a σ-complex in which the diene normally assumes a s-cis configuration in which the bond lengths between M and the four carbon atoms of the conjugated diene are significantly different (Δd<−0.15 Å). The formation of the complex with M in either the +2 or +4 formal oxidation state depends on the choice of the diene, the specific metal complex and the reaction conditions employed in the preparation of the complex.

Uniquely, where racemic or meso isomers may be produced (that is when the two Cp groups are optionally bonded together) the process results in formation of increased quantities of the racemic form of the diene metal complex. Typically, mixtures containing greater than 60 mole percent of the racemic isomer are produced.

It is to be understood that the present complexes may be formed and utilized as a mixture of the π-complexed and σ-complexed diene compounds where the metal centers are in the +2 or +4 formal oxidation state. Preferably the complex in the +2 formal oxidation state is present in a molar amount from 0.1 to 100.0 percent, more preferably in a molar amount from 10 to 100.0 percent, most preferably in a molar amount from 60 to 100.0 percent. Techniques for separation and purification of the complex in the +2 formal oxidation state from the foregoing mixtures are known in the art and disclosed for example in the previously mentioned Yasuda, I, supra, and Erker, I to III, supra, references and may be employed if desired to prepare and isolate the complexes in greater purity.

DETAILED DESCRIPTION

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

Useful dienes, D', are dienes that do not decompose under reaction conditions used to prepare the complexes according to the invention. Under subsequent polymerization conditions, or in the formation of catalytic derivatives of the present complexes, the diene ligand, D, may undergo chemical reaction or be replaced by another ligand.

Examples of suitable D ligands include: $\eta^4$-1,4-diphenyl-1,3-butadiene; $\eta^4$-1,3-pentadiene; $\eta^4$-1-phenyl-1,3-pentadiene; $\eta^4$-1,4-dibenzyl-1,3-butadiene; $\eta^4$-2,4-hexadiene; $\eta^4$-3-methyl-1,3-pentadiene; $\eta^4$-1,4-ditolyl-1,3-butadiene; $\eta^4$-1,4-bis(trimethylsilyl)-1,3-butadiene, 2,3 dimethyl butadiene, isoprene. Of the foregoing complexes, terminally substituted derivatives (that is, the 1,4-disubstituted 1,3-dienes and 1- or 4-monosubstituted 1,3-dienes) generally form π-complexes whereas solely internally substituted derivatives (that is, the 2,3-disubstituted 1,3-dienes and 2- or 3-monosubstituted 1,3-dienes) generally form σ-complexes. Examples of terminally substituted dienes include 1,4-diphenyl-1,3-butadiene, 1-phenyl-1,3-pentadiene, and 2,4 hexadiene. Examples of internally substituted dienes include isoprene or 2,3-dimethyl butadiene.

Preferred diene ligands are 1,3-pentadiene, 1,4-diphenyl-1,3-butadiene, 1-phenyl-1,3-pentadiene, 1,4-dibenzyl-1,3-butadiene, 2,4-hexadiene, 3-methyl-1,3-pentadiene, 1,4-ditolyl-1,3-butadiene, and 1,4-bis(trimethylsilyl)-1,3-butadiene. All geometric isomers the foregoing diene compounds may be utilized.

By the term "reducing agent" as used herein is meant a metal or compound which, under reducing conditions can cause the transition metal to be reduced from the +4 or +3 formal oxidation state to the +2 formal oxidation state. The same procedure is employed for the preparation of the diene complexes where M is in the +2 formal oxidation state or in the +4 formal oxidation state, the nature of formal oxidation state of M in the complex being formed being primarily determined by the diene employed. Examples of suitable metal reducing agents are alkali metals, alkaline earth metals, aluminum, zinc and alloys of alkali metals or alkaline earth metals such as sodium/mercury amalgam and sodium/potassium alloy. Specific examples of suitable reducing agent compounds are sodium naphthalenide, potassium graphite, lithium alkyls, aluminum trialkyls and Grignard reagents. Most preferred reducing agents are the alkali metals or alkaline earth metals, $C_{1-6}$ alkyl lithium, tri $C_{1-6}$ alkyl aluminum and $C_{1-6}$ alkyl Grignard reagents, especially lithium, n-butyl lithium, n-butyl MgCl, and triethyl aluminum.

The metal salts used as reactants in the present invention are preferably Group 4 metal halides, or dimethoxyethane (DME) or tetrahydrofuran (THF) adducts thereof, most preferably titanium tetrachloride, zirconium tetrachloride, hafnium tetrachloride, $ZrCl_4 \cdot 2THF$, or $HfCl_4 \cdot 2THF$.

By the term "mixtures" used with respect to Cp substituent groups are included Cp moieties bearing differing groups as well as Cp moieties bearing groups that are mixtures of the previously named entities, such as trihydrocarbylsilyl groups, especially trialkylsilyl groups, as well as trihydrocarbylgermyl groups, halohydrocarbyl groups and hydrocarbyloxy-substituted hydrocarbyl groups. Preferred substituents are $C_{1-6}$ hydrocarbyl or tri($C_{1-6}$ hydrocarbyl) silyl groups. Additionally preferably, component d) is a Grignard salt, lithium salt or trimethylsilyl derivative of Cp or Cp-Cp.

Preferred complexes formed by the present invention correspond to the formula:

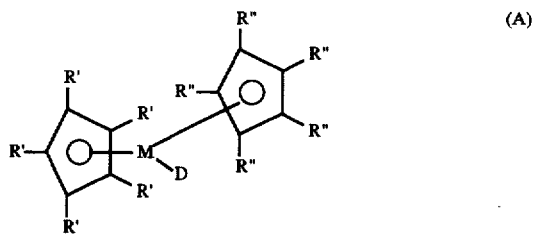

(A)

wherein:
M is titanium, zirconium or hafnium, preferably zirconium or hafnium, in the +2 or +4 formal oxidation state;
R' and R" in each occurrence are independently selected from the group consisting of hydrogen, hydrocarbyl, silyl, germyl, cyano, halo and combinations thereof, said R' and R" having up to 20 non-hydrogen atoms each, or adjacent R' groups and/or adjacent R" groups (when R' and R" are not hydrogen, halo or cyano) together form a divalent derivative (i.e., a hydrocarbadiyl, siladiyl or germadiyl group) or one R' and one R" together (when R' and R" groups are not hydrogen halo or cyano) combine to form a divalent radical (i.e., a hydrocarbadiyl, germadiyl or siladiyl group) linking the two substituted cyclopentadienyl groups; and D is as previously defined.

Preferably, R' and R" independently in each occurrence are selected from the group consisting of hydrogen, methyl, ethyl, and all isomers of propyl, butyl, pentyl and hexyl, as well as cyclopentyl, cyclohexyl, norbornyl, benzyl, and trimethyl silyl, or adjacent R' groups and/or adjacent R" groups on each cyclopentadienyl ring (except hydrogen) are linked together thereby forming a fused ring system such as an indenyl, 2-methyl-4-phenylindenyl, 2-methyl-4-naphthylindenyl, tetrahydroindenyl, fluorenyl, tetrahydrofluorenyl, or octahydrofluorenyl group, or one R' and one R" are linked together forming a 1,2-ethanediyl, 2,2-propanediyl or dimethylsilanediyl linking group.

Examples of the above metal complexes where the metal is titanium, zirconium or hafnium and preferably zirconium or hafnium include: bis($\eta^5$-cyclopentadienyl)zirconium ($\eta^4$-1,4-diphenyl-1,3-butadiene), bis(cyclopentadienyl) zirconium (2,3-dimethyl-1,3-butadiene), (bis-$\eta^5$-cyclopentadienyl)-zirconium $\eta^4$-1,4-ditolyl-1,3-butadiene, bis($\eta^5$-cyclopentadienyl)zirconium $\eta^4$-2,4-hexadiene, bis($\eta^5$-cyclopentadienyl)zirconium $\eta^4$-3-methyl-1,3-pentadiene, bis($\eta^5$-cyclopentadienyl)zirconium $\eta^4$-1-phenyl-1,3-pentadiene, bis(pentamethyl-$\eta^5$-cyclopentadienyl)zirconium $\eta^4$-1,4-diphenyl-1,3-butadiene, bis(pentamethyl-$\eta^5$-cyclo-Pentadienyl)zirconium $\eta^4$-1,4-dibenzyl-1,3-butadiene, bis(pentamethyl-$\eta^5$-cyclopentadienyl)zirconium $\eta^4$-2,4-hexadiene, bis(pentamethyl-$\eta^5$-cyclopentadienyl)zirconium $\eta^4$-3-methyl-1,3-pentadiene, bis(ethyltetramethyl-$\eta^5$-cyclopentadienyl) zirconium $\eta^4$-1,4-diphenyl-1,3-butadiene, bis(ethyltetramethyl-$\eta^5$-cyclopentadienyl)zirconium $\eta^4$-1,4-dibenzyl-1,3-butadiene, bis(ethyltetramethyl-$\eta^5$-cyclopentadienyl)zirconium $\eta^4$-2,4-hexadiene, bis (ethyltetramethyl-$\eta^5$-cyclopentadienyl)zirconium $\eta^4$-3-methyl-1,3-pentadiene, (pentamethyl-$\eta^5$-cyclopentadienyl), ($\eta^5$-cyclopentadienyl)zirconium $\eta^4$-1,4-dibenzyl-1,3-butadiene, ($\eta^5$-cyclopentadienyl)zirconium $\eta^4$-2,4-hexadiene, bis(t-butyl-$\eta^5$-cyclopentadienyl)-1,2-zirconium $\eta^4$-1,4-diphenyl-1,3-butadiene, bis(t-butyl-$\eta^5$-cyclopentadienyl)zirconium $\eta^4$-1,4-dibenzyl-1,3-butadiene, bis(t-butyltetramethyl-$\eta^5$-cyclopentadienyl)-zirconium $\eta^4$-2,4-hexadiene, $\eta^5$-cyclopentadienyl, (tetramethyl-$\eta^5$-cyclopentadienyl)zirconium $\eta^4$-3-methyl-1,3-pentadiene, bis(pentamethyl-$\eta^5$-cyclopentadienyl)zirconium $\eta^4$-1,4-diphenyl-1,3-butadiene, bis(pentamethyl-$\eta^5$-cyclopentadienyl)zirconium $\eta^4$-1-phenyl-1,3-pentadiene, bis-(tetramethyl-$\eta^5$-cyclopentadienyl)zirconium $\eta^4$-3-methyl-1,3-pentadiene, bis(methyl-$\eta^5$-cyclopentadienyl)zirconium $\eta^4$-1,4-diphenyl-1,3-butadiene, bis($\eta^5$-cyclopentadienyl)zirconium $\eta^4$-1,4-dibenzyl-1,3-butadiene, bis(trimethyl-silyl-$\eta^5$-cyclopentadienyl)zirconium $\eta^4$-2,4-hexadiene, bis(trimethylsilyl-$\eta^5$-cyclopentadienyl)-zirconium $\eta^4$-3-methyl-1,3-pentadiene, ($\eta^5$-cyclopentadienyl)(trimethylsilyl-$\eta^5$-cyclopentadienyl)zirconium $\eta^4$-1,4-diphenyl-1,3-butadiene, ($\eta^5$-cyclopentadienyl)(trimethylsilyl-$\eta^5$-cyclopentadienyl)zirconium $\eta^4$-1,4-dibenzyl-1,3-butadiene, (trimethylsilyl-$\eta^5$-cyclopentadienyl)(pentamethyl-$\eta^5$-cyclopentadienyl)zirconium $\eta^4$-2,4-hexadiene, bis(benzyl-$\eta^5$-cyclopentadienyl)zirconium $\eta^4$-3-methyl-1,3-pentadiene, bis($\eta^5$-indenyl)-zirconium $\eta^4$-1,4-diphenyl-1,3-butadiene, bis($\eta^5$-indenyl)zirconium $\eta^4$-1,4-dibenzyl-1,3-butadiene, bis($\eta^5$-indenyl)zirconium $\eta^4$-2,4-hexadiene, bis($\eta^5$-indenyl) zirconium $\eta^4$-3-methyl-1,3-pentadiene, bis($\eta^5$-fluorenyl) zirconium $\eta^4$-1,4-diphenyl-1,3-butadiene, (pentamethylcyclopentadienyl)($\eta^5$-fluorenyl)zirconium $\eta^4$-1-phenyl-1,3-pentadiene, bis($\eta^5$-fluorenyl)zirconium $\eta^4$-1,4-dibenzyl-1,3-butadiene, bis($\eta^5$-fluorenyl)-zirconium $\eta^4$-2,4-hexadiene, and bis($\eta^5$-fluorenyl)zirconium $\eta^4$-3-methyl-1,3-pentadiene.

Highly preferred bis-cyclopentadienyl compounds of formula A include those containing one or two bridging groups linking the cyclopentadienyl groups. Preferred bridging groups are those corresponding to the formula $(ER'''_2)_x$ wherein E is carbon, silicon or germanium, R''' independently each occurrence is hydrogen or a group selected from silyl, hydrocarbyl, hydrocarbyloxy and combinations thereof, or two R''' groups together form a ring system, said R''' having up to 30 carbon or silicon atoms, and x is an integer from 1 to 8. Preferably R''' independently each occurrence is methyl, benzyl, tert-butyl or phenyl.

Examples of the foregoing bridged cyclopentadienyl containing complexes are compounds corresponding to the formula:

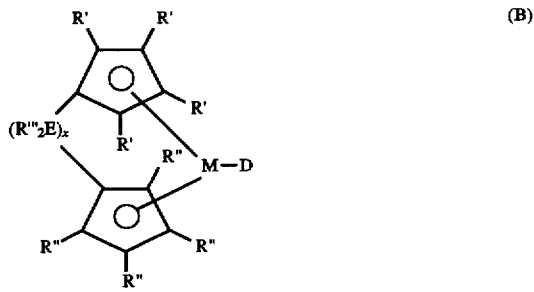

(B)

wherein:

M, D, E, R''' and x are as previously defined, and R' and R'' in each occurrence are independently selected from the group consisting of hydrogen, hydrocarbyl, silyl, germyl, cyano, halo and combinations thereof, said R' and R'' having up to 20 non-hydrogen atoms each, or adjacent R' groups and/or adjacent R'' groups (when R' and R'' are not hydrogen, halo or cyano) together form a divalent derivative (i.e., a hydrocarbadiyl, siladiyl or germadiyl group) or one R' and one R'' together (when R' and R'' groups are not hydrogen halo or cyano) combine to form a divalent radical (i.e., a hydrocarbadiyl, germadiyl or siladiyl group) linking the two cyclopentadienyl groups.

Such bridged structures are especially suited for the preparation of polymers having stereoregular molecular structure. In such capacity it is preferred that the complex be nonsymmetrical or possess a chiral, stereorigid structure. Examples of the first type are compounds possessing different delocalized π-bonded systems, such as one cyclopentadienyl group and one fluorenyl group. Similar systems based on Ti(IV) or Zr(IV) were disclosed for preparation of syndictactic olefin polymers in Ewen, et al., *J. Am. Chem. Soc.* 110, 6255–6256 (1980). Examples of chiral structures include bis-indenyl complexes. Similar systems based on Ti(IV) or Zr(IV) were disclosed for preparation of isotactic olefin polymers in Wild et al., *J. Organomet. Chem*, 232, 233–47, (1982).

Exemplary bridged cyclopentadienyl moieties in the complexes of formula (B) are: dimethylsilanediylbis((2-methyl-4-phenyl)-1-indenyl)zirconium ($\eta^4$-1,4-diphenyl-1,3-butadiene), dimethylsilanediyl-bis((2-methyl-4-(1-napthyl))-1-indenyl)zirconium ($\eta^4$-1,4-diphenyl-1,3-butadiene), 1,2-ethanediylbis(2-methyl-4-(1-phenyl)-1-indenyl)zirconium ($\eta^4$-1,4-diphenyl-1,3-butadiene), 1,2-ethanediyl-bis(2-methyl-4-(1-napthyl)-1-indenyl)zirconium ($\eta^4$-1,4-diphenyl-1,3-butadiene), [(1,2-ethanediylbis(1-indenyl)] zirconium ($\eta^4$-1,4-diphenyl-1,3-butadiene), [1,2-ethanediylbis(1-tetrahydroindenyl)]zirconium ($\eta^4$-1,4-diphenyl-1,3-butadiene), [1,2-ethanediylbis(1-indenyl)] hafnium ($\eta^4$-1,4-diphenyl-1,3-butadiene), and [2,2-propanediyl(9-fluorenyl)(cyclopentadienyl)]zirconium (1,4-diphenyl-1,3-butadiene).

In general, the process involves combining the respective reactants, preferably in a solution, optionally while agitating and heating above ambient temperature (25° C.). Recovery and purification of the intermediate products when a multiple step reaction is employed may be desirable. The process preferably is conducted in an inert, noninterfering solvent at a temperature from −100° C. to 300° C., preferably from −78° to 130° C., most preferably from −10° to 120° C.

Suitable inert, noninterfering solvents for the formation of the complexes are aliphatic and aromatic hydrocarbons and halohydrocarbons, ethers, and cyclic ethers. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, xylene, and the like, $C_{1-4}$ dialkyl ethers, $C_{1-4}$ dialkyl ether derivatives of (poly)alkylene glycols, and tetrahydrofuran. Mixtures of the foregoing list of suitable solvents are also suitable.

The recovery procedure involves separation of the resulting byproducts and devolatilization of the reaction medium. Extraction into a secondary solvent may be employed if desired. Alternatively, if the desired product is an insoluble precipitate, filtration or other separation technique may be employed.

The complexes are rendered catalytically active by combination with one or more activating cocatalysts, by use of an activating technique, or a combination thereof. Suitable activating cocatalysts include polymeric or oligomeric alumoxanes, especially methylalumoxane, triisobutyl aluminum modified methylalumoxane, or diisobutylalumoxane; strong Lewis acids (the term "strong Lewis acid" as used herein is defined as trihydrocarbyl substituted Group 13 compounds, especially tri(hydrocarbyl)aluminum- or tri (hydrocarbyl)boron compounds and halogenated derivatives thereof, having from 1 to 10 carbons in each hydrocarbyl or halogenated hydrocarbyl group, more especially perfluorinated tri(aryl)boron compounds, and most especially tris (pentafluorophenyl)borane); amine, phosphine, aliphatic alcohol and mercaptan adducts of halogenated tri($C_{1-10}$ hydrocarbyl)boron compounds, especially such adducts of perfluorinated tri(aryl)boron compounds; nonpolymeric, ionic, compatible, noncoordinating, activating compounds (including the use of such compounds under oxidizing conditions); bulk electrolysis (explained in more detail hereinafter); and combinations of the foregoing activating cocatalysts and techniques. The foregoing activating cocatalysts and activating techniques have been previously taught with respect to different metal complexes in the following references: EP-A-277,003, U.S. Pat. No. 5,153,157, U.S. Pat. No. 5,064,802, EP-A-468,651 (equivalent to U.S. Ser. No. 07/547,718), EP-A-520,732 (equivalent to U.S. Ser. No. 07/876,268), and WO93/23412 (equivalent to U.S. Ser. No. 07/884,966 filed May 1, 1992) the teachings of which are hereby incorporated by reference.

The catalysts may be used to polymerize ethylenically and/or acetylenically unsaturated monomers having from 2 to 20 carbon atoms either alone or in combination. Preferred monomers include the $C_{2-10}$ α-olefins especially ethylene, propylene, isobutylene, 1-butene, 1-hexene, 4-methyl-1-pentene, and 1-octene and mixtures thereof. Other preferred monomers include vinylcyclohexene, vinylcyclohexane, styrene, $C_{1-4}$ alkyl substituted styrene, tetrafluoroethylene, vinylbenzocyclobutane, ethylidenenorbornene, piperylene, 1,4-hexadiene, methyl-1,4-hexadiene and 7-methyl-1,6-octadiene.

When the present bridged cyclopentadienyl polymerization catalysts are used to polymerize prochiral olefins, syndiotactic or isotactic polymers are attainable. As used herein, the term "syndiotactic" refers to polymers having a stereoregular structure of greater than 50 percent, preferably greater than 75 percent syndiotactic of a racemic triad as determined by $^{13}C$ nuclear magnetic resonance spectroscopy. Conversely, the term "isotactic" refers to polymers having a stereoregular structure of greater than 50 percent, preferably greater than 75 percent isotactic of a meso triad as determined by $^{13}C$ nuclear magnetic resonance spectroscopy. Such polymers may be usefully employed in the preparation of articles and objects having an extremely high resistance to deformation due to the effects of temperature via compression molding, injection molding or other suitable technique.

EXAMPLE

Having described the invention the following examples are provided as further illustration thereof and are not to be construed as limiting. Unless stated to the contrary all parts and percentages are expressed on a weight basis.

EXAMPLE 1

Preparation of 1,2-ethanediylbis($\eta^5$-indenyl) zirconium (1,4-diphenyl-$\eta^4$-butadiene)

In an inert atmosphere glove box, 377 mg (1.00 mmol) of $ZrCl_4$, 106 mg (1.00 mmol) of 1,4-diphenyl-1,3-butadiene were combined in 60 ml of tetrahydrofuran (THF). To the stirred solution was added 0.80 ml (2.00 mmol) of 2.5M n-butyl lithium in mixed hexanes. The solution turned from colorless to bright orange. After two minutes 520 mg (1.00 mmol) of [1,2-ethylene bis(indenide)]($MgCl)_2(THF)_2$ was added as a solid. The solution turned dark red immediately.

After stirring at 25° C. for 3 hours, the volatiles were removed under reduced pressure. The red paste residue was triturated with mixed hexanes and extracted 3 times with a total of 60 ml of toluene. The extracts were filtered and combined with the hexanes filtrate and volatiles removed under reduced pressure. The solid residue was slurried in 2 mL of tetramethylsilane which was then decanted from the solid. Further drying under reduced pressure gave 286 mg of a red solid.

$^1H$ NMR analysis showed that racemic [1,2-ethylenebis (indenyl)]zirconium (1,4-diphenyl-1,3-butadiene) was the major product. Conversion to the dichloride by addition of concentrated HCl gave 63 percent of racemic [1,2-ethylenebis(indenyl)]zirconium dichloride and 37 percent of the meso isomer as the only identifiable indenyl containing products.

What is claimed is:

1. A process for preparing a metal complex containing two cyclopentadienyl groups or substituted cyclopentadienyl groups, said complex corresponding to the formula:

$$(Cp)_2MD$$

wherein:

M is titanium, zirconium or hafnium in the +2 or +4 formal oxidation state;

Cp independently each occurrence is a substituted or unsubstituted cyclopentadienyl group bound in an $\eta^5$ bonding mode to the metal, said substituted cyclopentadienyl group being substituted with from one to five substituents independently selected from the group consisting of hydrocarbyl, silyl, germyl, halo, cyano, hydrocarbyloxy, siloxy, and mixtures thereof, said substituent having up to 20 nonhydrogen atoms, or optionally, two such substituents (except cyano or halo) together cause Cp to have a fused ring structure, or together form one or two linking moieties joining the two Cp groups;

D is a stable, conjugated diene ligand, optionally substituted with one or more hydrocarbyl groups, silyl groups, hydrocarbylsilyl groups, silylhydrocarbyl groups, or mixtures thereof, said D having from 4 up to 40 nonhydrogen atoms and forming a π-complex with M when M is in the +2 formal oxidation state, and forming two π-bonds with M when M is in the +4 formal oxidation state, said process comprising contacting in any order:

a) a Group 4 metal salt corresponding to the formula M'$X_3$ or M"$X_4$, or a Lewis base adduct thereof, b) a conjugated diene, D', c) a reducing agent, and d) a compound of the formula: CpM* or (Cp-Cp)M*$_n$, wherein, M' is titanium, zirconium or hafnium in the +3 formal oxidation state;

M" is titanium, zirconium or hafnium in the +4 formal oxidation state;

X is a halide, $C_{1-6}$ hydrocarbyloxy or di($C_{1-6}$ hydrocarbyl) amido group;

D' is an uncoordinated diene having the same number of carbons as D and the same substitution pattern as D;

M* is a Group 1 or 2 metal cation, a Grignard reagent cation or a tri($C_{1-4}$ hydrocarbyl)silyl group; and n is 1 when M* is a Group 2 metal cation and n is 2 when M* is a Group 1 metal cation, a Grignard reagent cation, or a trihydrocarbylsilyl group with the proviso that reagents a), and d) are not contacted with one another in the absence of reagent c).

2. A process according to claim 1 wherein the Group 4 metal salt is a Group 4 metal chloride of a Lewis base adduct thereof.

3. A process according to claim 2 wherein the Group 4 metal salt is $ZrCl_4$, $ZrCl_4 \cdot 2THF$, $HfCl_4$ or $HfCl_4 \cdot 2THF$.

4. A process according to claim 1 wherein the diene is 1,3-pentadiene; 1,4-diphenyl-1,3-butadiene, 1-phenyl-1,3-pentadiene, 1,4-dibenzyl-1,3-butadiene, 2,4-hexadiene, 3-methyl-1,3-pentadiene, 1,4-ditolyl-1,3-butadiene, 1,4-bis-(trimethylsilyl)-1,3-butadiene, 2,3-dimethyl-1,3-butadiene, or isoprene.

5. A process according to claim 1 wherein the reducing agent is an alkali metal or alkaline earth metal, a $C_{1-6}$ alkyl lithium, a tri($C_{1-6}$ alkyl) aluminum compound or a Grignard reagent.

6. A process according to claim 5 wherein the reducing agent is n-butyl lithium, n-butyl MgCl, or $Al(Et)_3$.

* * * * *

UNITED STATES PATENT AND TRADEMARK OFFICE
CERTIFICATE OF CORRECTION

PATENT NO. : 5,679,816

DATED : October 21, 1997

INVENTOR(S) : Francis J. Timmers et al.

It is certified that error appears in the above-identified patent and that said Letters Patent is hereby corrected as shown below:

Column 8, line 46, "$\pi$-bonds" should correctly read --$\sigma$-bonds--.

Signed and Sealed this

Thirteenth Day of June, 2000

Attest:

Q. TODD DICKINSON

*Attesting Officer*  *Director of Patents and Trademarks*